(12) United States Patent
Raymond et al.

(10) Patent No.: US 9,161,688 B2
(45) Date of Patent: Oct. 20, 2015

(54) SYSTEM AND METHOD FOR CORNEAL PACHYMETRY USING PLENOPTIC IMAGING

(71) Applicant: AMO Waverfront Sciences, LLC., Santa Ana, CA (US)

(72) Inventors: Thomas D. Raymond, Albuquerque, NM (US); Richard J. Copland, Albuquerque, NM (US)

(73) Assignee: AMO Waverfront Sciences, LLC, Albuquerque, NM (US)

( * ) Notice: Subject to any disclaimer, the term of this patent is extended or adjusted under 35 U.S.C. 154(b) by 0 days.

(21) Appl. No.: 14/198,300

(22) Filed: Mar. 5, 2014

(65) Prior Publication Data

US 2014/0268043 A1     Sep. 18, 2014

Related U.S. Application Data

(60) Provisional application No. 61/793,510, filed on Mar. 15, 2013.

(51) Int. Cl.
*A61B 3/14* (2006.01)
*A61B 3/00* (2006.01)
*A61B 3/10* (2006.01)

(52) U.S. Cl.
CPC .............. *A61B 3/1005* (2013.01); *A61B 3/14* (2013.01)

(58) Field of Classification Search
CPC ............ A61B 3/14; A61B 3/12; A61B 3/103; A61B 3/152; A61B 3/113; A61B 3/1208; A61B 1/1225; A61B 1/024; A61B 3/032; A61B 3/1015

USPC ......... 351/206, 200, 205, 208–210, 221–223, 351/246, 211
See application file for complete search history.

(56) References Cited

U.S. PATENT DOCUMENTS

| | | |
|---|---|---|
| 4,665,913 A | 5/1987 | L'Esperance, Jr. |
| 4,669,466 A | 6/1987 | L'Esperance |
| 4,732,148 A | 3/1988 | L'Esperance, Jr. |
| 4,764,930 A | 8/1988 | Bille et al. |
| 4,770,172 A | 9/1988 | L'Esperance, Jr. |
| 4,773,414 A | 9/1988 | L'Esperance, Jr. |
| 5,108,388 A | 4/1992 | Trokel et al. |
| 5,163,934 A | 11/1992 | Munnerlyn |

(Continued)

FOREIGN PATENT DOCUMENTS

WO    WO 2010109020 A1 *  9/2010

*Primary Examiner* — Dawayne A Pinkney
(74) *Attorney, Agent, or Firm* — Abbott Medical Optics Inc.

(57) ABSTRACT

Embodiments described herein provide improved systems and methods for corneal pachymetry. These systems and methods can be used to improve the accuracy of corneal measurements that are used for a wide variety of different ophthalmic procedures. One embodiment provides a system and method for corneal pachymetry using a plenoptic detector. For example, a corneal pachymetry system can comprise a light source, a plenoptic detector and a processing system coupled to the plenoptic detector. The light source is configured to illuminate the cornea of the eye, and the plenoptic detector is positioned at an angle relative to the eye. The plenoptic detector is configured to receive an image of the light source reflected from the cornea and generate plenoptic image data representing the images. The processing system is coupled to the plenoptic detector and is configured to analyze the plenoptic image data to accurately determine the corneal thickness of the eye.

33 Claims, 7 Drawing Sheets

(56) References Cited

U.S. PATENT DOCUMENTS

| | | |
|---|---|---|
| 5,207,668 A | 5/1993 | L'Esperance, Jr. |
| 5,219,343 A | 6/1993 | L'Esperance, Jr. |
| 5,646,791 A | 7/1997 | Glockler |
| 5,993,438 A | 11/1999 | Juhasz et al. |
| 6,669,466 B2 | 12/2003 | Dijkstra et al. |
| 7,931,371 B2 | 4/2011 | Dai |
| 8,888,284 B2 | 11/2014 | Hogan |
| 9,060,710 B2 | 6/2015 | Copland |
| 2010/0004537 A1 | 1/2010 | Eilers et al. |
| 2011/0080561 A1 | 4/2011 | Hayashi et al. |
| 2011/0234977 A1* | 9/2011 | Verdooner .................... 351/207 |
| 2012/0069298 A1 | 3/2012 | Ng |
| 2013/0010260 A1* | 1/2013 | Tumlinson et al. ........... 351/206 |
| 2013/0027512 A1 | 1/2013 | Aronsson et al. |
| 2014/0268044 A1 | 9/2014 | Copland |
| 2014/0313515 A1 | 10/2014 | Hogan et al. |

* cited by examiner

SYSTEM AND METHOD FOR CORNEAL PACHYMETRY USING PLENOPTIC IMAGING

CROSS-REFERENCES TO RELATED APPLICATIONS

This application claims priority to U.S. provisional application No. 61/793,510 filed on Mar. 15, 2013, the entire contents of which are incorporated herein by reference.

TECHNICAL FIELD

Embodiments of the present invention generally relate to vision techniques, and particularly to techniques for corneal pachymetry.

BACKGROUND OF THE INVENTION

Many modern ophthalmic surgical procedures require accurate measurements of the eye. For example, measurements of aberrations of the eye are important for the diagnosis and treatment of visual defects and acuity. Furthermore, there are a growing number of ways that aberrations can be corrected using both surgical and non-surgical means. Many of these methods rely on accurate, precise measurements of the whole ocular system so that patients may be screened, the corrective means applied and tested, and follow up care provided as appropriate.

One important type of ocular measurement is referred to as corneal pachymetry. In general, corneal pachymetry is the measurement of the thickness of the cornea. The accurate measurement of corneal thickness is important for a variety of procedures. For example, many laser eye procedures require an accurate measurement of corneal thickness to determine if a patient can safely undergo the procedure. That is, if the corneal thickness is not within a specified limit the procedure cannot be performed. In those cases an inaccurate measurement can wrongly prevent patients from qualifying for the procedure. Or conversely, an inaccurate measurement can wrongly allow patients to undergo the procedure. In either case the safety and/or efficacy of the procedure can be comprised.

For these and other reasons there a continuing need for improved corneal pachymetry devices and techniques.

BRIEF SUMMARY OF THE INVENTION

Embodiments of the present invention generally provide improved systems and methods for corneal pachymetry. These systems and methods can be used to improve the accuracy of corneal measurements that are used for a wide variety of different ophthalmic procedures, including various types of ocular surgeries. One embodiment provides a system and method for corneal pachymetry using a plenoptic detector. For example, a corneal pachymetry system can comprise a light source, a plenoptic detector and a processing system coupled to the plenoptic detector. The light source is configured to illuminate the cornea of the eye, and the plenoptic detector is positioned at an angle relative to the eye. The plenoptic detector is configured to receive an image of the light source reflected from the cornea and generate plenoptic image data representing the images. The processing system is coupled to the plenoptic detector and is configured to analyze the plenoptic image data to accurately determine the corneal thickness of the eye.

Thus, the system and method can determine corneal pachymetry using a plenoptic detector. The use the plenoptic detector for corneal pachymetry can provide accurate measurement of corneal thickness.

To facilitate this, the plenoptic detector is configured to capture the intensity, position and direction of light hitting the detector. This information can be used to effectively refocus a plenoptic image at different focus depths after the image has been taken. The processing system can then use such a process to extract depth information from the plenoptic image. For example, by calculating distances between images reflected from different eye surfaces, such as different corneal surfaces. From this, the processing system determines corneal thickness for the eye.

The plenoptic detector includes a photosensor array comprising a plurality of photosensors and a microlens array comprising a plurality of lenslets. The microlens array is configured to receive images of the light sources reflected from surfaces of the eye and direct the images to the photosensor array. Such an arrangement allows the plenoptic detector to determine both the intensity and the direction of light hitting the detector.

In one specific example, the set of light sources are configured to illuminate the eye with a slit of light. In another embodiment the set of light sources are configured to rotate relative to the eye.

The above summary and the following detailed description are merely exemplary, illustrative, and explanatory, and are not intended to limit, but to provide further explanation of the invention as claimed. Additional features and advantages of the invention will be set forth in the ensuing detailed descriptions that follow, and in part, will be apparent from the description, or may be learned by practicing various embodiments of the invention. The objectives and other advantages of the invention will be realized by the structures and methods particularly pointed out in the written description and claims as well as the accompanying drawings.

DETAILED DESCRIPTION OF THE INVENTION

The figures and descriptions of the present invention have been simplified to illustrate elements that are relevant for a clear understanding of the present invention, while eliminating, for the purpose of clarity and brevity, many other elements found in typical ophthalmic techniques, systems, methods, lenses, and implantable optic apparatuses. Those of ordinary skill in the art may thus recognize that other elements and/or steps are desirable and/or required in implementing the present invention. However, because such elements and steps are well known in the art, and because they do not necessarily facilitate a better understanding of the present invention, those elements and steps are not discussed. This disclosure is directed to all applicable variations, changes, and modifications known to those skilled in the art. As such, the following detailed descriptions are merely illustrative and exemplary in nature and are not intended to limit the embodiments of the subject matter or the uses of such embodiments.

As used in this application, the terms "exemplary" and "illustrative" mean "serving as an example, instance, or illustration." Any implementation described as exemplary or illustrative is not meant to be construed as preferred or advantageous over other implementations. Further, there is no intention to be bound by any expressed or implied theory presented in the preceding background of the invention, brief summary, or the following detailed description.

Embodiments of the present invention generally provide improved systems and methods for corneal pachymetry. These systems and methods can be used to improve the accuracy of corneal measurements that are used for a wide variety of different ophthalmic procedures, including various types of ocular surgeries. One embodiment provides a system and method for corneal pachymetry using a plenoptic detector. For example, a corneal pachymetry system can comprise a light source, a plenoptic detector and a processing system coupled to the plenoptic detector. The light source is configured to illuminate the eye, and the plenoptic detector is positioned at an angle relative to the eye. The plenoptic detector is configured to receive images of the light source reflected from corneal surfaces of the eye and generate plenoptic image data representing the images. The processing system is coupled to the plenoptic detector and is configured to analyze the plenoptic image data to accurately determine the corneal thickness of the eye.

Thus, the system and method can determine corneal pachymetry using a plenoptic detector. The use the plenoptic detector for corneal pachymetry can provide accurate measurement of corneal thickness.

To facilitate this, the plenoptic detector is configured to capture the intensity, position and direction of light hitting the detector. This information can be used to effectively refocus a plenoptic image at different focus depths after the image has been taken. The processing system can then use such a process to extract depth information from the plenoptic image. For example, by calculating distances between images reflected from different eye surfaces, such as different corneal surfaces. As another example, by calculating the distance from the cornea to the plenoptic detector. From this, the processing system determines corneal thickness for the eye.

Figure 1:
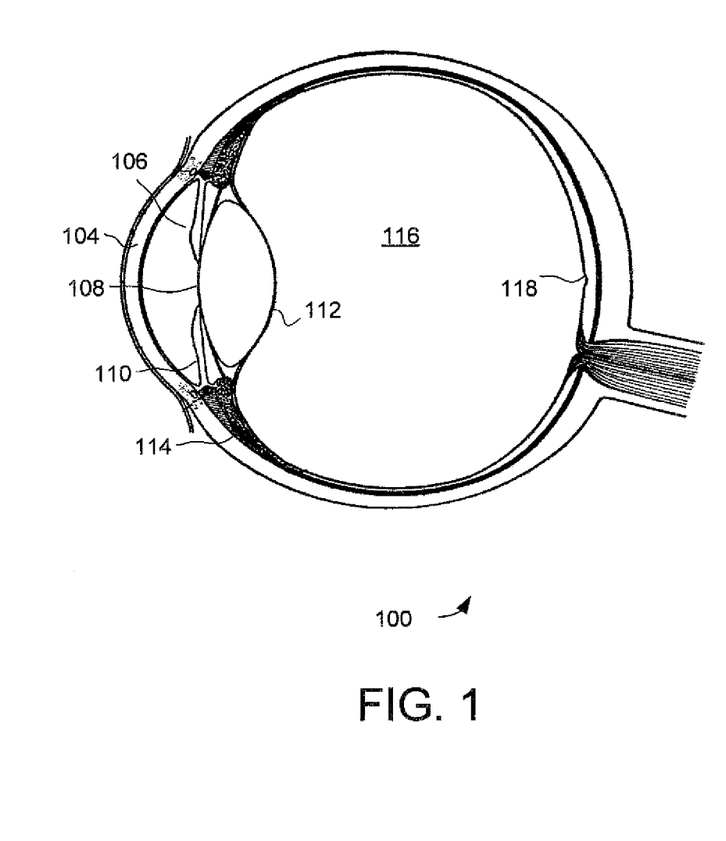
FIG. 1 is a cross-sectional side view of a human eye.

Turning to the drawings. FIG. 1 illustrates a simplified cross-sectional view of an exemplary human eye 100. In general, the eye 100 includes a cornea 104, an anterior chamber 106, a pupil 108, an iris 110, a lens 112, a ciliary muscle 114, a posterior chamber 116, and a retina 118. As briefly described earlier, many modern ophthalmic procedures require accurate measurements of the eye. For example, many laser eye surgery procedures require accurate measurement of the thickness of cornea 104 to determine whether a patient is a suitable candidate for the procedure.

Figure 2:
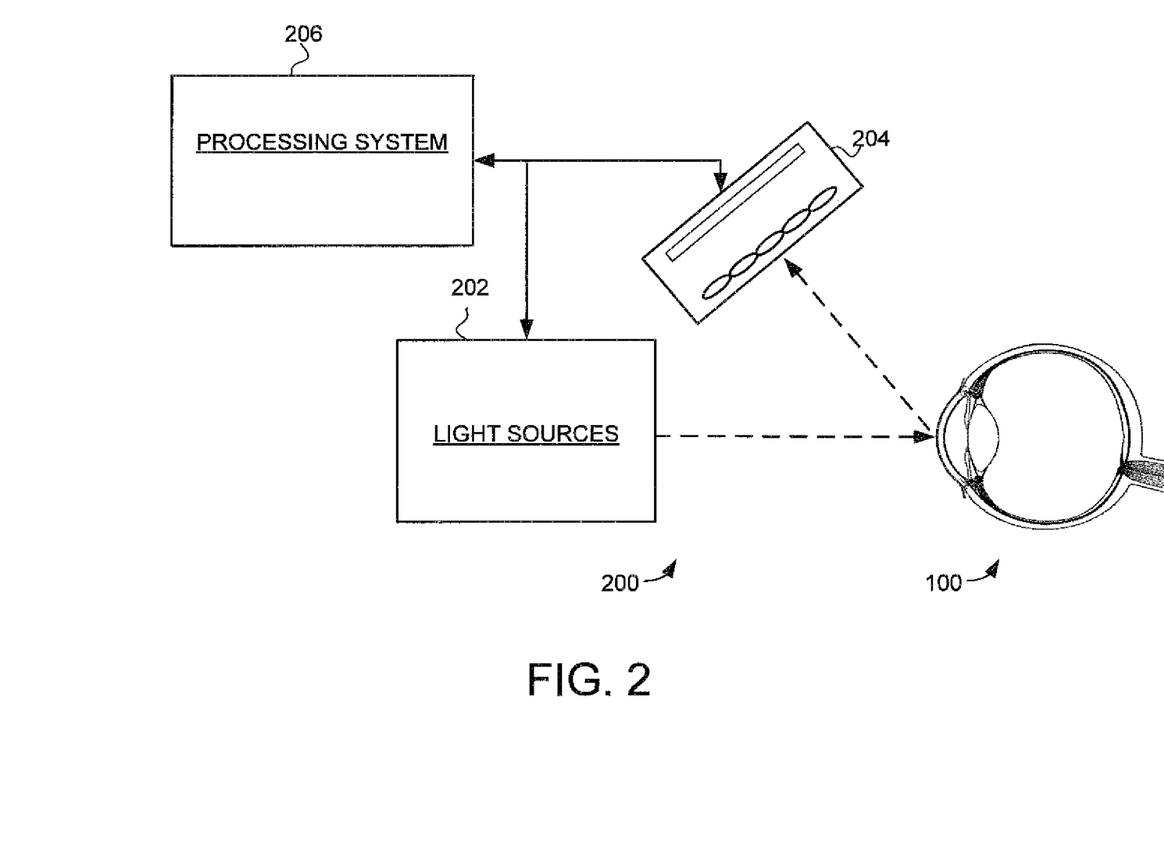
FIG. 2 is a schematic diagram of a corneal pachymetry system in accordance with an embodiment of the invention.

Turning now to FIG. 2, a simplified schematic view of a corneal pachymetry system 200 is illustrated. The system 200 includes light sources 202, a plenoptic detector 204, and a processing system 206. In general, the light sources 202 and associated optical elements (not shown in FIG. 2) are configured to illuminate the eye 100 with a set of light sources. For example, the light generator 202 can comprise a light source configured to illuminate the eye with a slit shaped image. For example, a slit shaped image of blue light. As will be described in greater detail below, other suitable light sources can be used as well. Furthermore, the light sources 202 can be configured to rotate about the eye 100.

In general, the plenoptic detector 204 is positioned at an angle relative to the eye and is configured to detect the resulting images scattered from the eye 100. Such a configuration allows the system 200 to use the Scheimpflug principle in determining corneal thickness. Specifically, the plenoptic detector 204 is configured to determine both intensity and direction of light scattered from the eye 100 and hitting the detector. This information can be used to effectively refocus a plenoptic image at different focus depths after the image has been captured, and this refocusing can be used to extract depth information. Furthermore, this information can be used to virtually tilt a plenoptic image to be more accurately in the correct plane for Scheimpflug orientation.

As one example implementation, the plenoptic detector 204 can include a photosensor array comprising a plurality of photosensors and a microlens array comprising a plurality of microlenses that are referred to as lenslets. In such a configuration the microlens array is configured to receive images of the light sources 202 reflected from surfaces of the eye 100 and direct the images to the photosensor array. From this, the plenoptic detector 204 can calculate both intensity and direction of light hitting the plenoptic detector 204.

In the embodiment shown in FIG. 2, the light sources 202 and plenoptic detector 204 are each coupled to processing system 206. The processing system 206 is configured to control the light sources 202 and plenoptic detector 204. Additionally, the processing system 206 is configured to analyze the plenoptic image data to determine corneal pachymetry data for the eye 100. As described above, the plenoptic detector 204 is configured to capture the intensity, position and direction of light hitting the detector. The processing system 206 can use this plenoptic image data to refocus captured images at different focus depths after the images have been taken. The processing system 206 can then use such a process to extract depth information from the plenoptic image. For example, the processing system 206 can be implemented to calculate distances between images reflected from different eye surfaces, such as different corneal eye surfaces, and can be used to calculate the distance from the cornea to the plenoptic detector. From this, the processing system 206 can determine the corneal thickness of the eye.

For example, the plenoptic data can be analyzed by the processing system 206 to calculate a distance to the cornea. For example, by processing system 206 using the plenoptic image data to computationally refocus an image scattered from the apex of the cornea. It should be noted that in this case the light that scatters from the cornea can be viewed directly by the plenoptic detector 204, and is not a virtual image that is viewed through the corneal surface. This provides a good reference point for measuring the distance to the cornea.

As another example, the plenoptic image data can be processed to virtually "tilt" the plane of the image relative to the eye. As will be described in more detail below, the computational tilting of an image captured by the plenoptic detector 204 can be used to precisely control the angle of tilt of the resulting image relative to the surface of the cornea, and thus can be used adjust a virtual plane of focus. For example, by computationally tilting the plenoptic image relative to the eye to more accurately correspond to a Scheimpflug orientation angle. This can facilitate a more accurate use of the Scheimpflug principle to calculate corneal thickness. Furthermore, the plenoptic image data can be processed to determine corneal thickness of the eye by computationally focusing the images of the light source scattered from the corneal surfaces of the eye. For example, the corneal thickness can be determined by calculating corneal curvatures based on a computational focusing of the images scattered from the cornmeal surfaces of the eye.

To facilitate these actions the processing system 206 can comprise any suitable configuration of processing elements, including various computer memories, controllers, and other devices. For example, the processing system 206 can be implemented as software residing in memory and being executed by a processor, or as hardware hardcoded into a processing device, or any combination thereof.

The light sources 202 can comprise any source of electromagnetic radiation, particularly a source in or near the visible band of the electromagnetic spectrum, for example, in the infrared, near infrared, or ultraviolet bands of the electromagnetic radiation. Furthermore, as used herein, the term "light" may be extended to mean electromagnetic radiation in or near the visible band of the electromagnetic spectrum, for example, in the infrared, near infrared, or ultraviolet bands of the electromagnetic radiation, or to mean electromagnetic radiation detectible by a photodetector or electromagnetic image sensor (e.g., CCD) or that is otherwise useful in measuring the optical or physical characteristics of an object under examination.

As was described above, the light sources 202 can comprise a light source configured to illuminate the eye with a slit shaped pattern. For example, a slit shaped pattern of blue light. However, this is just one example, and other types of light sources could be used instead of, or in addition to such a slit shaped light source. As other examples the light sources 202 can include a pattern that includes a plurality of common elements having a common form and one or more reference elements having a reference form that is different than the common form. As a specific example, the slit shaped pattern can include a pattern of variation, such as a variation from brighter to dimmer regions. In such a case this variation in pattern and knowledge regarding the spacing of the variation in pattern can be used to increase accuracy of the measurement.

In another variation the eye is illuminated with an array pattern, such as a "checkerboard" pattern. As an example, a number of bundles of light such that the light pattern covered an area across the pupil can be used in addition to or instead of the slit. Finally, different colors and polarizations of illuminating light can also be used.

As used herein, the term "form", when applied to an element or object, means a shape and orientation of the element or object, without regard to its scale or dimension. As used herein the term "different", when applied to a comparison between two or more "forms", means the forms being compared have a different shape and/or orientation in comparison to one another. As used herein the term "same", when applied to a comparison between two or more "forms", means the forms being compared have equivalent shape and orientation in comparison to one another.

It should further be noted that the use of the plenoptic detector 204 allows the use of a larger aperture which can collect light much more efficiently than detectors typically used in a Scheimpflug configuration. Specifically, with conventional Scheimpflug configurations the tilted object plane is not a perfect match to the fixed sensor tilt so the lens typically must have a relatively small aperture. Such a configuration can lead to errors generated by the non-ideal sensor tilt. Furthermore, the use of a larger aperture can facilitate the use of lower light levels, which can improve patient comfort and safety.

The system 200 can be implemented as a stand-alone device or as part of a larger diagnostic system or a larger ophthalmic laser system. For example, the system 200 can be implemented as part of an ophthalmic diagnostic and/or measurement system designed to provide one or more of wavefront aberrometry, topography, autorefractometry, pupillometry, and optical coherence topography and aberrometry. More specifically, the system 200 may be incorporated into and implemented as part of the WaveScan WaveFront® System or the iDesign Advanced WaveScan Studio® System, both by Abbott Medical Optics Inc. an ophthalmic diagnostic and measurement system that uses a Shack-Hartmann wavefront sensor to quantify aberrations throughout the entire optical system of the patient's eye, including second-order aberrations related to spherical error and cylindrical errors and higher order aberrations related to coma, trefoil, and spherical aberrations. An exemplary wavefront diagnostic system is described in U.S. Pat. No. 7,431,371, issued to Dai, which is incorporated by reference in its entirety.

Alternatively, the system 200 may be incorporated into and implemented as part of a device or system that is used to generate pulsed laser beams, including non-ultraviolet (non-UV), ultrashort pulsed laser beams that have pulse durations that are measured in femtoseconds, as described in U.S. Pat. Nos. 4,764,930 and 5,993,438. Certain non-UV, ultrashort pulsed laser systems are used for ophthalmic surgeries. For example, U.S. Pat. No. 5,993,438 discloses a laser device for performing ophthalmic surgical procedures to effect high-accuracy corrections of optical aberrations. Further details of suitable systems for performing laser ophthalmic procedures can be found in commonly-assigned U.S. Pat. Nos. 4,665,913, 4,669,466, 4,732,148, 4,770,172, 4,773,414, 5,207,668, 5,108,388, 5,219,343, 5,646,791 and 5,163,934.

As described above, the system 200 can be configured to use the Scheimpflug principle in determining corneal thickness. In general, the Scheimpflug principle is a geometric rule that describes the orientation of the plane of focus of an optical system when the lens plane is not parallel to the image plane.

In a typical normal camera the plane of focus for the detector is parallel to the lenses and image planes. In contrast, in a typical Scheimpflug orientation the object plane and the image plane intersect with the lens plane. This orientation of the object plane, lens plane, and image plane allows the object to be in focus on the image plane even though the object plane is not parallel with image plane. The Scheimpflug orientation between object plane and image plane is used in corneal thickness determination, specifically to measure cornea shape and thickness. Specifically, when a narrow slit of light is projected onto the cornea the light is scattered by the cornea where the slit of light is passing through it. This creates a crescent shaped scattering object. A detector that is positioned at an angle relative to the cornea corresponding to the Scheimpflug orientation can capture a good image of the shape scattering object. Specifically, the Scheimpflug orientation of the detector and object creates a situation where a good image of the object may be captured and used for corneal thickness determination.

However, the quality of the image captured by a detector in the Scheimpflug orientation depends upon the precise placement of the detector in the correct plane. Thus, these devices must be tightly calibrated. The embodiments described herein provide the ability to virtually control the angle of the detector using the plenoptic image data. Specifically, the intensity and direction information provided by the plenoptic detector can be used to virtually "tilt" the image relative to the eye by processing the image data. This virtually tilting is performed such that the resulting image corresponds to an image more precisely aligned in the correct plane for Scheimpflug orientation. The computational tilting of an image captured by the plenoptic detector 204 can be used to precisely control the angle of tilt of the resulting image relative to the surface of the cornea, and thus can be used more precisely focus the image can be accomplished using purely mechanical techniques. Furthermore, such techniques can be used to adjust the virtual tilt of the image to compensate for variations in corneal dimensions. For example, by computationally tilting the plenoptic image data relative to the eye to more accurately correspond to a Scheimpflug angle relative to the corneal surfaces. This can facilitate a more accurate use of the Scheimpflug principle to calculate corneal thickness.

Figure 3:
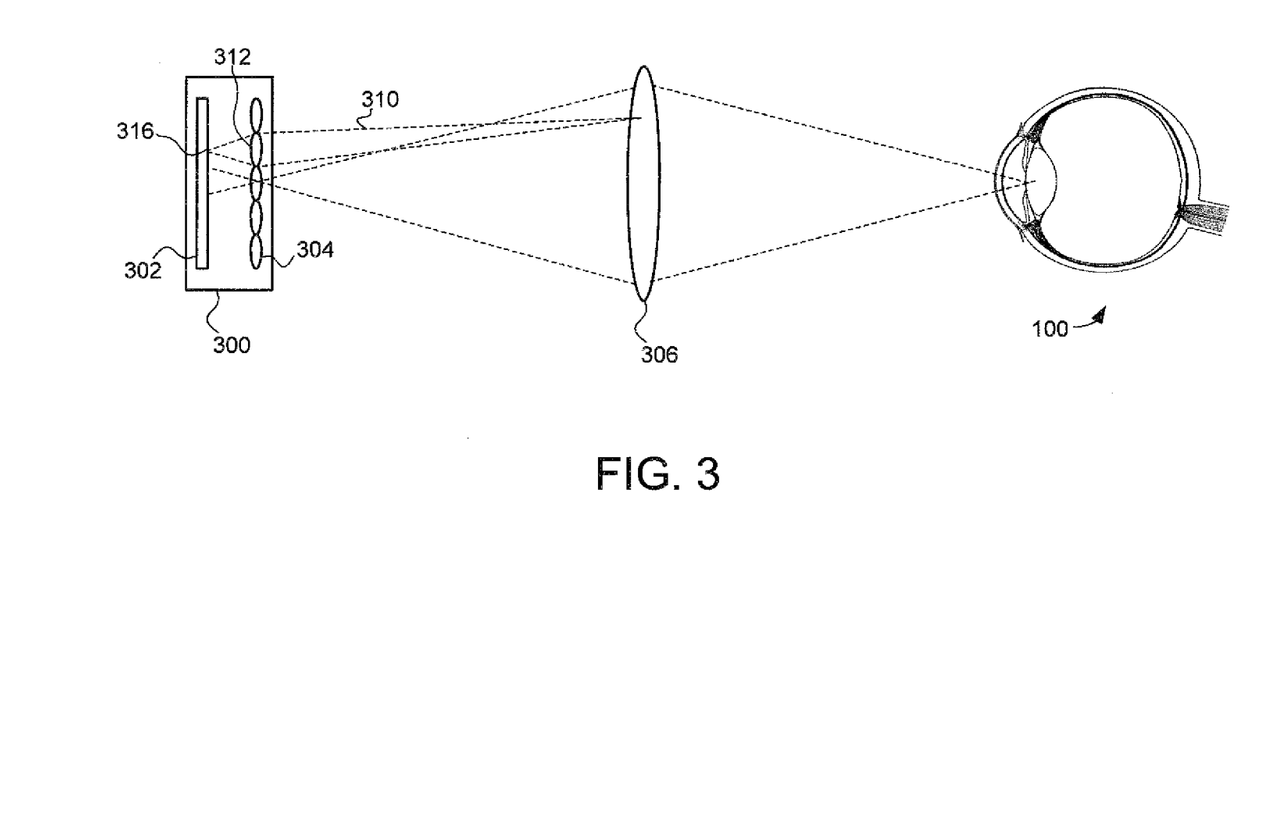
FIG. 3 is a schematic diagram of a plenoptic detector and eye in accordance with an embodiment of the invention.

Turning now to FIG. 3, a plenoptic detector 300 is illustrated schematically. The plenoptic detector 300 includes a photosensor array 302 comprising a plurality of photosensors and a microlens array 304 comprising a plurality of microlenses, with individual microlenses sometimes referred to as lenslets. In the illustrated embodiment, the microlens array 304 is configured to receive images of the light sources (not shown in FIG. 3) reflected from surfaces of the eye 100 and directed to the detector 300 with lens 306. In general, each lenslet in the microlens array 304 covers multiple sensors or "pixels" in the photosensor array 302. As will be described in greater detail below, this results in reduced spatial resolution, but also provides the ability to determine direction information for incident light hitting the plenoptic detector 300.

Turning now to FIG. 3, a plenoptic detector 300 is illustrated schematically. The plenoptic detector 300 includes a photosensor array 302 comprising a plurality of photosensors and a microlens array 304 comprising a plurality of microlenses, with individual microlenses sometimes referred to as lenslets. In the illustrated embodiment, the microlens array 304 is configured to receive images of the light sources (not shown in FIG. 3) reflected from surfaces of the eye 100 and directed to the detector 300 with lens 306. In general, each lenslet in the microlens array 304 covers multiple sensors or "pixels" in the photosensor array 302. As will be described in greater detail below, this results in reduced spatial resolution, but also provides the ability to determine direction information for incident light hitting the plenoptic detector 300.

A variety of different types of devices can be used for the photosensor array 302 in the plenoptic detector 300. For example, the individual photosensors can be implemented with digital imaging devices such as a charge coupled detector (CCD). As another example, the photosensors can be implemented with active pixel sensors. Likewise, the microlens array can be implemented in a variety of different ways. For example, the microlens array can be manufactured by photolithographic or molding processes. Furthermore, different relative positioning between the various elements can be used. For example, in some plenoptic detectors 300 the microlens array 304 is positioned to be in the image plane of the main lens 306. Conversely, in other examples the microlens array 304 is positioned to be in front of or behind the image plane of the main lens 306. Likewise, different relative positioning between the microlens array 304 and the photosensor array 302 can be used. For example, the photosensor array 302 may be positioned one lenslet focal length behind the microlens array 304.

Next, it should be noted that because each lenslet in microlens array 304 covers multiple pixels in the photosensor array 302, the resulting images captured by the photosensor effectively have reduced spatial image resolution, while adding the ability to determine directional information. As one example, each lenslet in the microlens array 304 may correspond to 100 pixels in the photosensor array 302. In such an embodiment the resulting images would be reduced in spatial resolution by two orders of magnitude. Again, this is just one example, and in other cases each lenslet could correspond to more or less pixels on the photosensor array 302. For example, some plenoptic detectors 300 may use 10 pixels per lenslet in the microlens array 302, and would thus have less reduction in resolution. However, such plenoptic detectors 300 would also provide reduced directional information. And while the reduction in resolution may be considered undesirable for some applications, the embodiments describe herein use such plenoptic image data to determine information about an eye that could not be determined with an ordinary camera regardless of the increased resolution.

In general, the plenoptic detector 300 as illustrated in FIG. 3 is configured to determine both intensity and direction of light reflecting from the eye 100 and hitting the detector 300. To accomplish this, the lens 306 is configured to direct light reflected from surfaces of the eye 100 to the microlens array 304. The microlens array 304 is configured to receive this light and direct that light to the photosensor array 302. From this, the plenoptic detector 300 can calculate both the intensity and direction of the light reflected from the eye 100.

In general, each lenslet in the microlens array 304 receives light from the eye at a different angle than the other lenslets in the array, and each photosensor in the photosensor array 302 receives a different view of the eye from each lenslet in the array of microlenses 304, and wherein each different view of the eye is received at a separate location on the photosensor array 302 to produce a multidimensional array of different views of the eye at the photosensor array 302. Stated another way, each lenslet in the microlens array 304 receives light from the eye at different angles and spatially separates the light at different angles at the photosensor array 302. Stated another way, wherein each lenslet in the microlens array 304 is configured such that light arriving at a point in different directions is directed at a different point on the photosensor array 302 such that direction information for light ray can be determined from a position of the light ray Conventional cameras capture two-dimensional images, with each pixel in the image representing the total amount of light striking each point in the camera sensor. Notably, a conventional two-dimensional image does not include any information about the direction any of the light was traveling when it hit the sensor. In contrast, a plenoptic detector such as detector 300 captures information on the directional distribution of the light rays.

Specifically, the microlens array 304 enables the plenoptic detector 300 to capture the light-field, i.e. to record not only image intensity, but also the distribution of intensity in different directions at each point. Specifically, the rays at the microlens array 304 have different angles, and passing through a lenslet causes rays with different angles to separate. Thus, each lenslet in the microlens array 304 splits a beam coming to it from the main lens 306 into different rays, and each of these different rays hits a different pixel on photosensor array 302. The result is a multipixel image formed under each lenslet in the microlens array 304, with the multipixel image containing measurements of different angular samples of the incident light at the lenslet. This multipixel area under each lens may be referred to as a "macropixel", and the plenoptic detector 300 effectively generates a "microimage" at each such macropixel. For example, a plenoptic detector with 100,000 lenslets in the microlens array 304 will contain 100,000 macropixels, and thus generate 100.000 microimages.

An example of this is illustrated in FIG. 3, which shows rays 310 hitting lenslet 312 in microlens array 304, and subsequently hitting a point 316 on photosensor array 302. For clarity, only rays through lenslet 312 are illustrated, but other rays through different lenslets would also fall at different pixels on the photosensor array 302. The result is a microimage at each macropixel, and the raw image data of the plenoptic detector 300 could thus be considered an array of such microimages.

Stated another way, each lenslet in the microlens array 304 functions to convert directional or angular information into positional information that is captured at the photosensor array 302. Because of this conversion, the position of a ray at the photosensor array 302 provides directional or angular information about the ray. Thus, the measurements taken at the pixels in the photosensor array 302 can be used to provide both directional and intensity data regarding light reflected from the eye 100. And such measurements, as a set of such plenoptic image data, can be used form an image by selecting appropriate pixels from each microimage. Furthermore, by mixing pixels from different microimages images at different focus depths that can be generated. This different focus depth can be used to refocus images, determine distances to an between images, or can further be used to computationally tilt an image to more accurately correspond to a particular plane, such as to virtually tilt and image to the Scheimpflug orientation angle.

Figure 4:
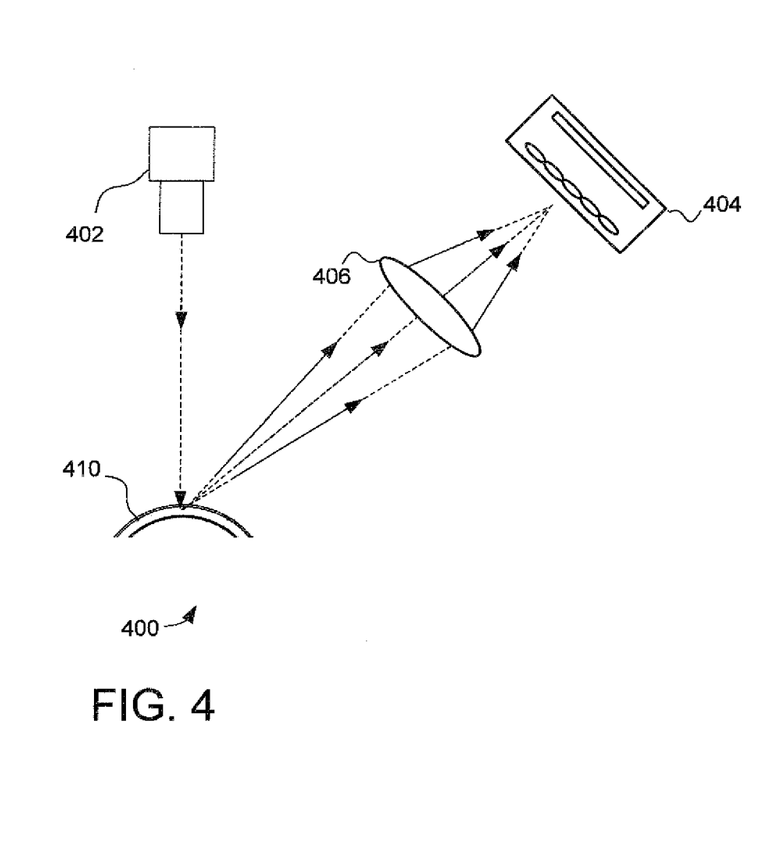
FIGS. 4-7 are schematic diagrams of corneal pachymetry systems in accordance with embodiments of the invention.

Turning now to FIG. 4, a simplified schematic view of corneal pachymetry system 400) is illustrated. The system 400 includes a light source 402, a plenoptic detector 404, and a lens 406. Not shown is a processing system that would be coupled to at least the plenoptic detector 404. In general, the light source 402 and the lens 406 are configured to illuminate the cornea 410 of the eye. In this case the light source 402 can comprise light emitting diodes (LEDs) or other such light sources as discussed above.

In general, the plenoptic detector 404 is positioned at an angle relative to the eye and is configured to detect the resulting images scattered from a volume of tissue from inside the cornea 410. Such a configuration allows the system 200 to use the Scheimpflug principle in determining corneal thickness. Specifically, the plenoptic detector 204 is configured to determine both intensity and direction of light scattered from the eye 100 and hitting the detector. This information can be used to effectively refocus a plenoptic image at different focus depths after the image has been captured, and this refocusing can be used to extract depth information. Furthermore, this information can be used to virtually tilt a plenoptic image to be more accurately in the correct plane for Scheimpflug orientation. That is, the relative focus of difference portions of the image are recalculated and changed to correspond to what the image would look like had the detector being more precisely in the correct plane for Scheimpflug orientation.

In FIG. 4 the dashed lines represent light rays going from the scattering volume of the cornea 410 to the plenoptic detector 404. For simplicity. FIG. 4 does not show how the object that is viewed by the plenoptic detector 404 is actually a virtual object that is displaced slightly from the scattering volume of the cornea 410.

As described above, the plenoptic detector 404 can include a photosensor array comprising a plurality of photosensors and a microlens array comprising a plurality of microlenses that are referred to as lenslets. In such a configuration the microlens array is configured to receive an image of the light source 402 as scattered and reflected from the cornea 410 and directed by lens 406. The image of the light source 402 is passed by the microlens array to the photosensor array. From this, the plenoptic detector 404 can calculate both intensity and direction of light hitting the plenoptic detector 404. From this intensity and light information the relative focus of difference portions of the image can be recalculated to virtually change the "tilt" plane of the image. This computationally calculated change in virtual tilt of the image plane effectively generates the image that would have been captured originally if a corresponding detector had been positioned in that plane. Thus, the changing of the virtual plane of the image can be used to correct for misalignment in the detector or variations that occur due to changes in cornea shape and/or size. In either case the image can be modified to more accurately correspond to the correct Scheimpflug orientation between cornea 410, lens 406 and plenoptic detector 404.

This ability for virtual tilting of the image plane can provide various different advantages over traditional techniques. For example, in the embodiment illustrated in FIG. 4, the plenoptic detector is essentially perpendicular to the lens 406. Such an arrangement does not correspond to the Scheimpflug orientation and thus would be less than ideal with a regular detector. However, the ability to virtually change the "tilt" plane of the image allows such an orientation to be used and the plenoptic image data to be processed to generate an image on the correct plane for Scheimpflug orientation.

As another example, because plenoptic data taken with the plenoptic detector 404 can be used to calculate an image as it would have been taken on the tilted image plane from a single measurement, the plenoptic detector 404 is not required to move while the light source 402 is being scanned to make highly accurate measurements. This can result in a significant simplification in mechanical design relative to other such devices.

Figure 5:
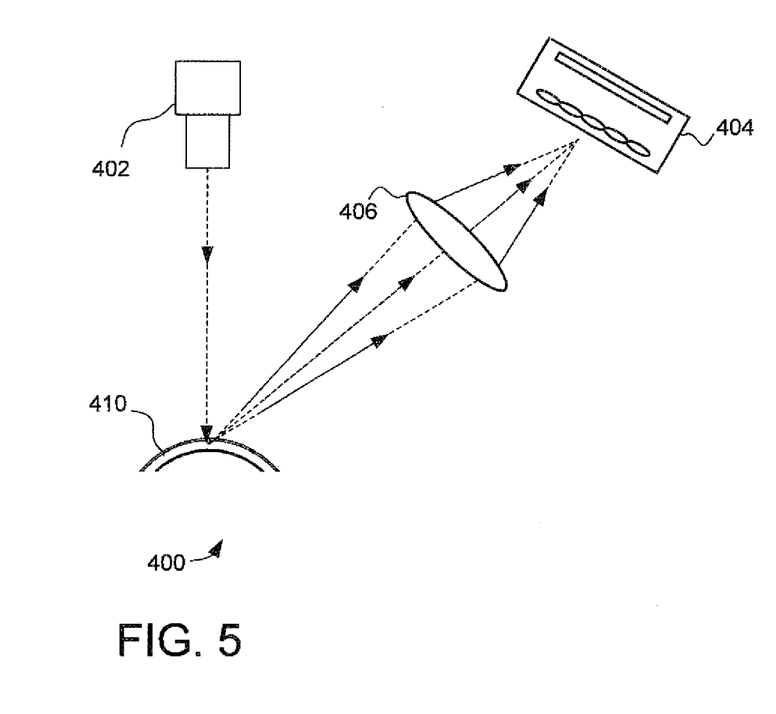

Turning now to FIG. 5, a second simplified schematic view of corneal pachymetry system 400 is illustrated. This illustration is similar to FIG. 4, but with the variation that the plenoptic detector 404 is positioned at an angle closer to the correct Scheimpflug orientation. Specifically, the plenoptic detector has been rotated at an angle relative to the position of the lens 406 and cornea 410. Configuring the plenoptic detector 404 such that the detector is positioned at an angle closer to the correct Scheimpflug orientation provides the potential benefit of requiring less computational tilting of the image plane to virtually move the plane to the correct orientation. Furthermore, this can allow for more precise tilting of the image plane as the originally detected image will be of higher quality.

Figure 6:
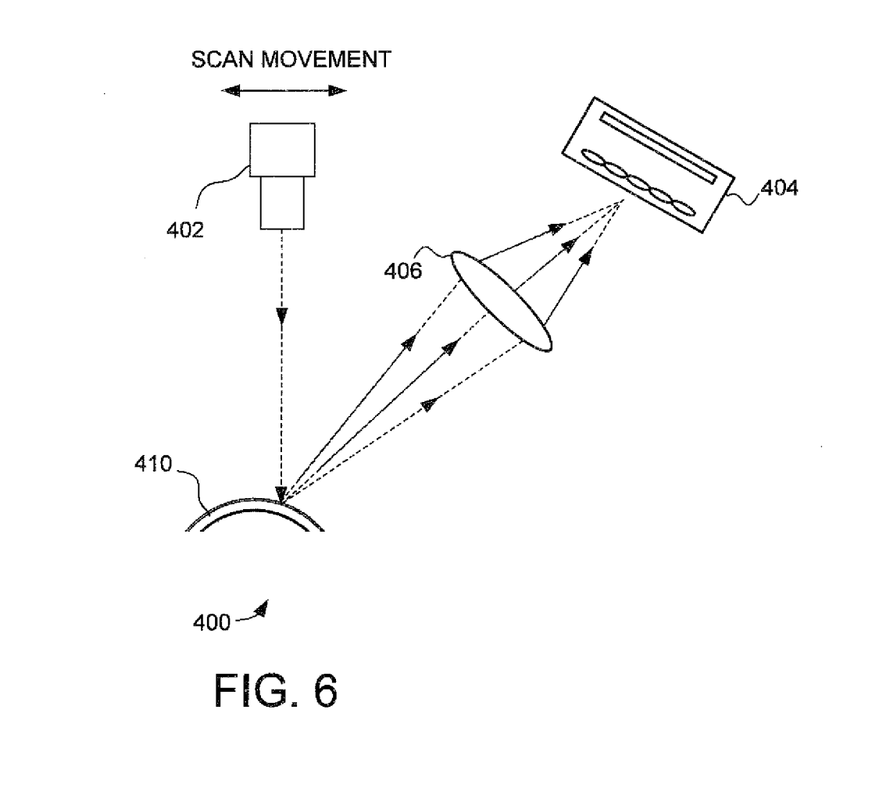

Turning now to FIG. 6, third simplified schematic view of corneal pachymetry system 400 is illustrated. This illustration is similar to FIGS. 4 and 5, but shows how the light source 402 can be configured to change output position and scan over the cornea 410. Such an arrangement allows the system 400 to accurately measure the thickness of a larger portion of cornea 410. Furthermore, in this embodiment the ability to virtually change the "tilt" plane of the image captured by detector 404 can avoid the need for detector 404 to also move to compensate for the change in position of the light source 402. Stated another way, the plenoptic image data can be processed to generate images on the correct planes for Scheimpflug orientation as the light source 402 moves along to scan over the eye. This again can result in increased accuracy and/or range for the system 400.

And again, because image data from plenoptic detector 404 can be used to calculate such titled image planes, the plenoptic detector 404 is not required to move while the light source 402 is being scanned. This again can result in a significant simplification in mechanical design relative to other such devices.

Figure 7:
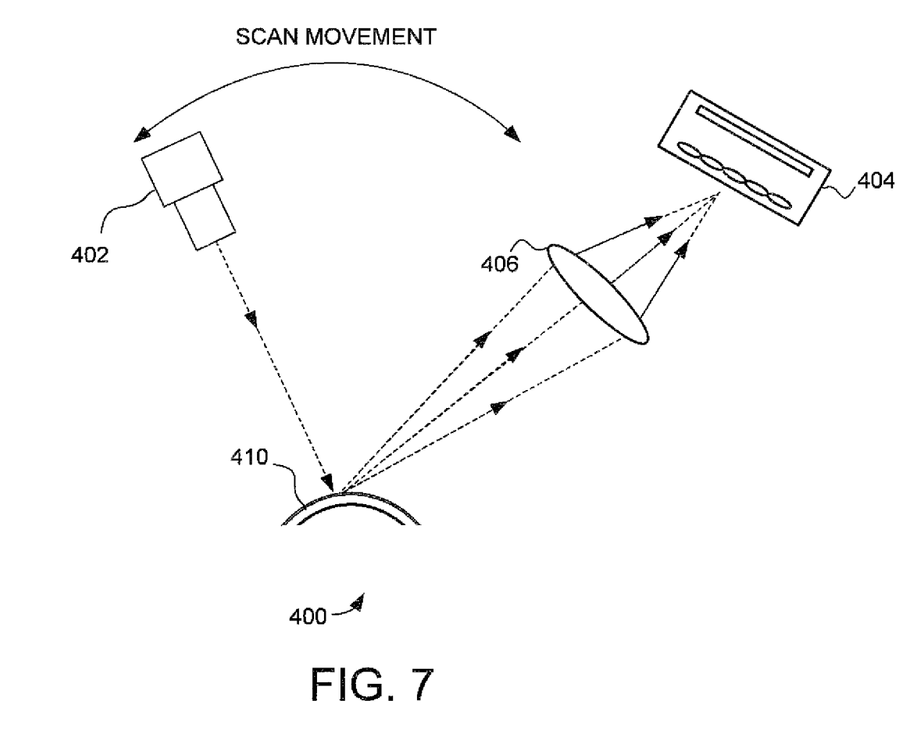

Turning now to FIG. 7, fourth simplified schematic view of corneal pachymetry system 400 is illustrated. This illustration is similar to FIGS. 4, 5 and 6, but in this case shows how the light source 402 can be configured to change output position by rotating around the eye in an arc. Again, the ability to scan change output position and scan over the cornea 410 can provide the ability to accurately measure the thickness of a larger portion of cornea 410. Furthermore, in this embodiment the ability to scan by following an arc makes allows the beam of light outputted by the light source 402 to stay nearly perpendicular to the surface of the cornea at each point along the scan. This can reduce the amount of warping of the virtual object that is created by scattering from the cornea 410 and detected by the plenoptic detector 404. And again, the ability to virtually change the tilt plane of the image captured by detector 404 can avoid the need for detector 404 to also move to compensate for the change in position of the light source 402. Stated another way, the plenoptic image data can be processed to generate images on the correct planes for Scheimpflug orientation as the light source 402 moves along the arc. This can result in increased accuracy and/or range for the system 400.

The embodiments described herein thus provide techniques for accurate determination of corneal thickness. Such techniques can be used for any ophthalmic procedure requiring accurate determinations. These techniques can thus be used to improve the effectiveness of a wide variety of different ophthalmic procedures. Furthermore, it should be noted that while the use of a plenoptic detector has been described with reference to determining corneal thickness by computationally adjusting the tilt of images for Scheimpflug orientation, that the embodiments described herein could be applied to other measurements. For example, techniques of using the plenoptic detector and computationally adjusting the tilt of images for Scheimpflug orientation could be applied to the measuring of any structure or object where light shows scattering through a volume.

This disclosure has been provided in an exemplary form with a certain degree of particularity, and describes the best mode contemplated of carrying out the invention to enable a person skilled in the art to make or use embodiments of the invention. Those skilled in the art will understand, however, that various modifications, alternative constructions, changes, and variations can be made in the system, method, and parts and steps thereof, without departing from the spirit or scope of the invention. Hence, the disclosure is not intended to be limited to the specific examples and designs that are described. Rather, it should be accorded the broadest scope consistent with the spirit, principles, and novel features disclosed as generally expressed by the following claims and their equivalents.

What is claimed is:

1. A corneal pachymeter system, the corneal pachymeter system comprising:
    a light source configured to illuminate a cornea of an eye;
    a plenoptic detector, the plenoptic detector positioned at an angle relative to the eye, the plenoptic detector configured to detect both intensity and direction of light of an image of the light source scattered from the cornea and generate plenoptic image data representing the image including both the intensity and the direction of the light detected by the plenoptic detector; and
    a processing system coupled to the plenoptic detector, the processing system configured to:
        analyze the plenoptic image data to determine corneal thickness of the eye by computationally tilting the image of the light source derived from the plenoptic image data to more accurately correspond to a Scheimpflug orientation angle.

2. The system of claim 1 wherein the plenoptic image detector comprises:
    a photosensor array, the photosensor array comprising a plurality of photosensors; and
    a microlens array, the microlens array comprising a plurality of lenslets configured to direct the image to the photosensor array, the microlens array arranged a predetermined distance from the photosensor array.

3. The system of claim 2 wherein the photosensor array comprises a two dimensional array of photosensors, and wherein the microlens array comprises a two dimensional array of lenslets.

4. The system of claim 2 wherein the photosensor array is arranged in an image plane.

5. The system of claim 2 wherein each lenslet in the microlens array receives light from the eye at different angles and spatially separates the light at different angles at the detector.

6. The system of claim 2 wherein each lenslet in the microlens array is configured such that light arriving at a point in different directions is directed at a different point on the photosensor array such that direction information for light ray can be determined from a position of the light ray.

7. The system of claim 1 wherein the light source is configured to output a slit shaped pattern of light.

8. The system of claim 1 wherein the light source is configured change output position to scan over the eye.

9. The system of claim 1 wherein the plenoptic detector is configured to rotate relative to the eye.

10. The system of claim 1 wherein the light source is configured to change output position to scan over the eye and the plenoptic detector are configured to rotate relative to the eye.

11. The system of claim 1 wherein the plenoptic detector is configured to change the angle relative to the eye.

12. The system of claim 1 wherein the processing system is configured to analyze the plenoptic image data to determine corneal thickness of the eye by calculating distance to the cornea using the plenoptic data.

13. The system of claim 12 wherein the processing system is configured to calculate the distance to the cornea using the plenoptic data by computationally focusing the image scattered from the cornea.

14. The system of claim 12 wherein the processing system is configured to calculate the distance to the cornea using the plenoptic data by computationally focusing a virtual image that is scattered from an apex of the cornea.

15. The system of claim 1 wherein the processing system is configured to analyze the plenoptic image data to determine corneal thickness of the eye by computationally tilting the plenoptic image data relative to the eye.

16. The system of claim 1 wherein the processing system is configured to analyze the plenoptic image data to determine corneal thickness of the eye by computationally focusing the image of the light source scattered from the cornea of the eye.

17. The system of claim 1 wherein the processing system is configured to analyze the plenoptic image data to determine corneal thickness of the eye by calculating corneal curvature by computationally focusing the image of the light source scattered from the corneal surfaces of the eye.

18. A corneal pachymeter system, the corneal pachymeter system comprising:
    a light source configured to output a slit of light to illuminate an eye and scatter an image of the light source from the cornea;
    a plenoptic detector, the plenoptic detector positioned at an angle relative to the eye, the plenoptic detector configured to detect both intensity and direction of light of the scattered image of the light source and generate plenoptic image data representing the scattered image including both the intensity and the direction of the light detected by the plenoptic detector; and a processing system coupled to the plenoptic detector, the processing system configured to analyze the plenoptic image data to:
- calculate distance to the cornea using the plenoptic data by computationally focusing a virtual image that is scattered from an apex of the cornea;
- computationally tilting the image of the light source to more accurately correspond to a Scheimpflug orientation angle;
- calculating corneal curvatures by computationally focusing the computationally tilted image of the light source; and
- calculating a thickness of the cornea from the calculated distance to the cornea and the calculated corneal curvatures.

19. A method for determining thickness of a cornea in an eye, the method comprising:
- illuminating the cornea of the eye with a light source;
- detecting both intensity and direction of light of an image of the light source scattered from the cornea with a plenoptic detector positioned at an angle relative to the eye;
- generating plenoptic image data representing the image including both the intensity and the direction of the light detected by the plenoptic detector; and
- analyzing the plenoptic image data to determine corneal thickness of the cornea by computationally tilting the image of the light source derived from the plenoptic image data to more accurately correspond to a Scheimpflug orientation angle.

20. The method of claim 19 wherein the plenoptic image detector comprises:
- a photosensor array, the photosensor array comprising a plurality of photosensors; and
- a microlens array, the microlens array comprising a plurality of lenslets configured to direct the image to the photosensor array, the microlens array arranged a predetermined distance from the photosensor array.

21. The method of claim 20 wherein the photosensor array comprises a two dimensional array of photosensors, and wherein the microlens array comprises a two dimensional array of lenslets.

22. The method of claim 20 wherein the photosensor array is arranged in an image plane.

23. The method of claim 20 wherein each lenslet in the microlens array receives light from the eye at different angles and spatially separates the light at different angles at the detector.

24. The method of claim 20 wherein each lenslet in the microlens array is configured such that light arriving at a point in different directions is directed at a different point on the photosensor array such that direction information for light ray can be determined from a position of the light ray.

25. The method of claim 19 wherein the illuminating the cornea of the eye with a light source comprises illuminating the eye with a slit of light.

26. The method of claim 19 further comprising rotating the plenoptic detector relative to the eye while illuminating the eye and receiving images of the light source scattered from corneal surfaces of the eye.

27. The method of claim 19 further comprising changing output position to scan over the eye while receiving images of the light source scattered from corneal surfaces of the eye.

28. The method of claim 19 wherein further comprising changing an angle of the plenoptic detector relative to the eye.

29. The method of claim 19 wherein analyzing the plenoptic image data to determine corneal thickness of the eye comprises calculating distance to the cornea using the plenoptic data.

30. The method of claim 19 wherein analyzing the plenoptic image data to determine corneal thickness of the eye comprises computationally focusing a virtual image that is scattered from an apex of the cornea.

31. The method of claim 19 wherein analyzing the plenoptic image data to determine corneal thickness of the eye comprises computationally tilting the plenoptic image data relative to the eye.

32. The method of claim 19 wherein analyzing the plenoptic image data to determine corneal thickness of the eye comprises computationally focusing the image of the light source scattered from the cornea.

33. The method of claim 19 wherein analyzing the plenoptic image data to determine corneal thickness of the eye comprises calculating corneal curvature by computationally focusing the image of the light source scattered from the cornea.

* * * * *